(12) United States Patent
Ferrari

(10) Patent No.: US 7,507,217 B2
(45) Date of Patent: Mar. 24, 2009

(54) DEVICE FOR EXCHANGING AND/OR DOCKING FUNCTIONAL MODULES

(75) Inventor: Markus Ferrari, Jena (DE)

(73) Assignee: PPA Technologies AG, Jena (DE)

( * ) Notice: Subject to any disclaimer, the term of this patent is extended or adjusted under 35 U.S.C. 154(b) by 26 days.

(21) Appl. No.: 10/592,287

(22) PCT Filed: Mar. 9, 2005

(86) PCT No.: PCT/EP2005/002505

§ 371 (c)(1), (2), (4) Date: Sep. 8, 2006

(87) PCT Pub. No.: WO2005/087290

PCT Pub. Date: Sep. 22, 2005

(65) Prior Publication Data

US 2007/0208292 A1    Sep. 6, 2007

(30) Foreign Application Priority Data

Mar. 9, 2004 (DE) .................. 10 2004 011 461

(51) Int. Cl.
| | |
|---|---|
| A61M 37/00 | (2006.01) |
| A61B 19/00 | (2006.01) |
| B01D 29/00 | (2006.01) |
| C02F 9/00 | (2006.01) |
| E03B 11/00 | (2006.01) |
| F17D 1/00 | (2006.01) |

(52) U.S. Cl. .................. 604/6.16; 604/6.09; 604/6.1; 604/406; 210/253; 210/254; 210/255; 210/261; 137/265; 137/266

(58) Field of Classification Search .............. 604/6.09, 604/6.1, 7, 4.01, 5.01, 403; 210/252, 253, 210/254, 255, 257.7, 261, 262, 457, 199, 210/200, 201, 203, 232; 422/44–48; 137/833, 137/838, 219, 256, 259, 266, 265

See application file for complete search history.

(56) References Cited

U.S. PATENT DOCUMENTS 3,834,372 A    9/1974   Turney (Continued)

FOREIGN PATENT DOCUMENTS

| DE | 10 2004 001 861 A1 | 1/2004 |
|---|---|---|
| EP | 0 704 227 A2 | 9/1995 |

OTHER PUBLICATIONS

Online dictionary entry for "bypass" accessed Dec. 3, 2007. http://www.askoxford.com/concise_oed/bypass?view=uk.*

(Continued)

*Primary Examiner*—Leslie Deak
*Assistant Examiner*—Adam Marcetich
(74) *Attorney, Agent, or Firm*—Fraser Clemens Martin & Miller LLC; J. Douglas Miller

(57) ABSTRACT

A device for exchanging and/or docking functional modules (1, 2), and used for the extracorporeal circulation of bodily fluids, is provided. Each functional module (1, 2) includes at least one conduit (3; 4) comprising an inlet (5; 7) and an outlet (6; 8). The aim of the invention is to exchange the functional modules of an extracorporeal circuit as rapidly as possible, without detaching tubular connections and without having to establish a new connection. The invention is provided with elements (9, 10; 11, 12) for connecting the conduit (3) of a first functional module (1) to the inlet (5) and the outlet (6) of a second functional module (2). The connection is established in such a way that the first functional module (1) is bypassed by means of the second functional module (2) to maintain the flow and the bodily fluid is diverted through the second functional module (2).

8 Claims, 2 Drawing Sheets

U.S. PATENT DOCUMENTS

Figure 1:
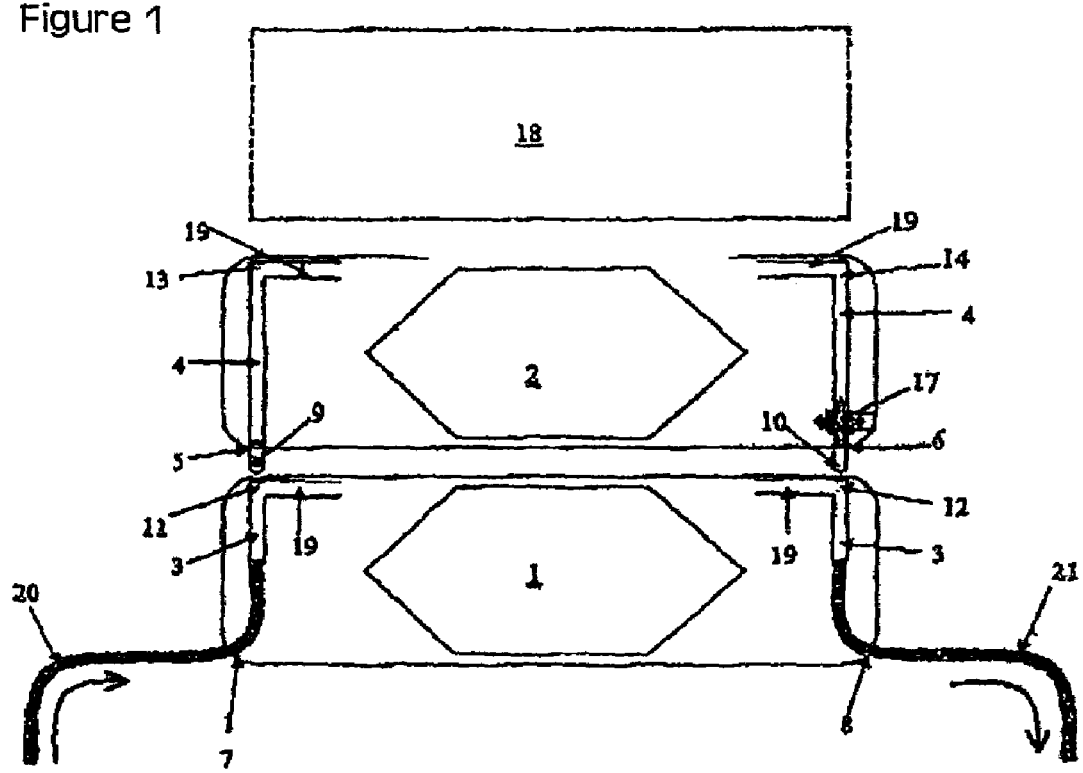

| | | | | |
|---|---|---|---|---|
| 3,986,960 | A | * | 10/1976 | Wire et al. .................. 210/232 |
| 4,192,750 | A | * | 3/1980 | Elfes et al. .................. 210/133 |
| 4,228,012 | A | * | 10/1980 | Pall ............................ 210/238 |
| 4,371,438 | A | * | 2/1983 | Benattar et al. ............. 210/232 |
| 4,828,543 | A | * | 5/1989 | Weiss et al. ................ 604/6.09 |
| 5,108,598 | A | * | 4/1992 | Posner ........................ 210/232 |
| 5,141,637 | A | * | 8/1992 | Reed et al. .................. 210/232 |
| 5,342,518 | A | * | 8/1994 | Posner et al. ............... 210/232 |
| 5,407,571 | A | * | 4/1995 | Rothwell ..................... 210/232 |
| 5,435,915 | A | * | 7/1995 | Connors, Jr. ................ 210/232 |
| 5,651,887 | A | * | 7/1997 | Posner et al. ............... 210/232 |
| 5,662,642 | A | * | 9/1997 | Isono et al. ................. 604/403 |
| 5,895,570 | A | * | 4/1999 | Liang ......................... 210/232 |
| 6,042,721 | A | * | 3/2000 | Peters et al. ................. 210/85 |
| 6,139,741 | A | * | 10/2000 | McGibbon ................ 210/323.1 |
| 6,241,945 | B1 | | 6/2001 | Owens |
| 6,349,835 | B1 | * | 2/2002 | Saux et al. .................. 210/427 |
| 6,403,008 | B1 | * | 6/2002 | Schann ....................... 264/255 |
| 6,467,481 | B1 | * | 10/2002 | Eswarappa ............. 128/206.17 |
| 7,186,337 | B2 | * | 3/2007 | Reid ........................... 210/232 |
| 2002/0179512 | A1 | * | 12/2002 | Axelrod ..................... 210/169 |
| 2003/0102257 | A1 | * | 6/2003 | Reid ........................... 210/232 |

OTHER PUBLICATIONS

Online dictionary definition of "intervene." http://www.merriam-webster.com/cgi-bin/dictionary?book=Dictionary&va=intervene. Accessed Jul. 7, 2008.*

* cited by examiner

DEVICE FOR EXCHANGING AND/OR DOCKING FUNCTIONAL MODULES

The submitted invention concerns a device for changing and/or docking of functional modules for the extra corporeal circulation of body fluids wherein each functional module has at least one of the body fluid permeable conduits with an inlet and an outlet.

When using machines through which blood or sterile fluids flow (for example, in administering of medications) it is known how to make conduit links by use of the connecting tubes or thread adapters. This is especially necessary for hemodialysis or also for operating heart and lung machines, wherein special care must be taken for a sufficient sterility of the connections. Accordingly, these known systems for extra corporeal circulation are hiding in them the danger of a blood secretion into the surrounding environment or a germ penetration into the perfusion system and thus into the patient's circulation during its use on the patient. During the switching over from one of the functional modules of the perfusion system into an additional or another module (for example in changing the dialysis filters during the hemodialysis or the oxygen generators of the heart lung machines) must generally take place very fast, since the damage to the patient with a consecutive functional failure of the perfusion system (for example, thrombus buildup or an air permeation) can be expected. For that reason, it has been established for a case of an obstructed filter during a chronic hemodialysis, that the entire perfusion system, including the taps, adapters, etc must be changed. That means, nevertheless, that the device must be disconnected from the patient's circulation with the corresponding danger of infection or loss of blood (the blood in the connecting tubes cannot be fully re-infused) and lost time in therapy. Additionally, in case of changing the entire set, that is to say, the connecting tubes and the remanent components of the circulation, additional costs are incurred. In the use of a heart-lung machine which, in case of an interruption of the patient's heart function, must continue to operate without stopping, a change of a defective membrane oxygen generator represents a dangerous maneuver.

Against the background of this problem, the task of the submitted invention is based in the need to change the functional module of an extra corporeal circulation as fast as possible and without detachment of the tube connections and without having to attach a corresponding new connection.

The task will be solved with a device for changing and/or docking of a functional module of the initially named type in accordance with the invention by a component for connecting the conduit of the first functional module with the input and the output of a second functional module in that the first functional module will be bridged by using fluid mechanics to divert the body fluid through the second functional module.

The advantages of the solution, according to the invention, lie especially in that during the running of the extra corporeal circulation, a bypass of the body fluid flow from an old (first) functional module to a new (second) functional module is established. Thus the substitution of the functional modules in the extra corporeal circulation can take place without switching the tube connections and without interrupting the circulation. Thus, the device according to the invention has a great advantage in that the change of the functional module can take place in the shortest possible time, while the switching of the tube connections in case of the known devices, even in the hands of the best trained cardiology technician can lead to a standstill of the heart-lung machine of up to two minutes. This can certainly be avoided with the use of the submitted invention.

Advantageous design developments of the invention are provided in the sub claims. Preferably, each of the connecting elements comprises valve connections for the input and output of the second functional module as well as a designated portal on the conduit of the first functional module, wherein the valve connections engage the functional module in the respectively assigned portals so that the functional circulation of the first functional module is bridged over. Thus the connecting valves, in the manner of plug-type connectors, make the connection between the old (first) and the new (second) functional module and thus bypass the blood flow under sterile conditions. Hereby it permits the positioning of the attachment points for the valve connections a multiple substitution of a used or a defective (first) functional module by a new (second) functional module. The second functional module and any additional one, the latter again substituting a functional module, then functions as a bypass to the used or, as the case may be, (first) functional module being substituted.

While the valve connections for input and output of the second functional module can be fundamentally rated as individual components of consumption material, it is preferably planned that the input and the output of the second functional module each of which is designed with valve connections which, when the functional module with the accordingly designed portals is joined together, combine in making a leak-proof body fluid permeable connection. Thus a second or any additional functional module already bears structurally both of the valve connections whose standardized arrangement takes care that in mounting, the valve connections of the second and any additional functional module intervene without any other action and thus establish rapidly and without problems the connection with the functional modules in the designated portals of the first fuinctional module and thus establish the by-pass of the functional circulation of the first or, as the case may be, any previous functional module.

Should it become necessary to attach an additional functional module to the second functional module, it has been designed in an advantageous way so that the second functional module is also designed for connection with additional functional modules and also provided with portals. Thus the substitution of functional modules can similarly take place multiple times due to the module configuration.

To take care that every one of the portals is outwardly sealed germ free, two alternatives have been foreseen, according to the invention: First, under unused conditions, each of the portals can be sealed at the outward leading end with a penetrable membrane, or else this can be accomplished by means of a valve. Furthermore, both arrangements can also be kept germ free or even sterile by a protective cap, a foil, or by some other covering. Also a combination of the three above noted possibilities could be considered.

The outlet of the second functional module or, as the case may be, any additional functional module, can preferably be provided with a priming valve for air release from the second functional module or, as the case may be, from additional functional modules for filling it with a fluid. This priming valve can, of course, be also used for administration of medications.

For any structural implementation of connecting the functional module which diverts the circulation of the body fluid through a second functional module and, at the same time, discontinuing the circulation through the first functional module, two alternative solutions are foreseen according to the invention: First, each portal can comprise an angled branching of the respective conduits so that during the penetration in the respective conduit, the branching section closes each valve connection and diverts the flow of the body fluid into the second functional module or, as the case may be, into any additional functional modules. This is the simplest and, at the same time, most dependable structural design that must be grasped by the cardiology technician or physician, since no other intervention for diverting the circulation need to be used and, furthermore, it represents the fastest way of making the connection. And second, it can also be expected that each portal comprises a valve mechanism in the form of a three way valve located in the branching, which can then be switched into the circulation after the attachment of a second functional module.

In the following text, we will clarify in detail the preferred design examples of the invention shown in the illustrations.

Figure 2:
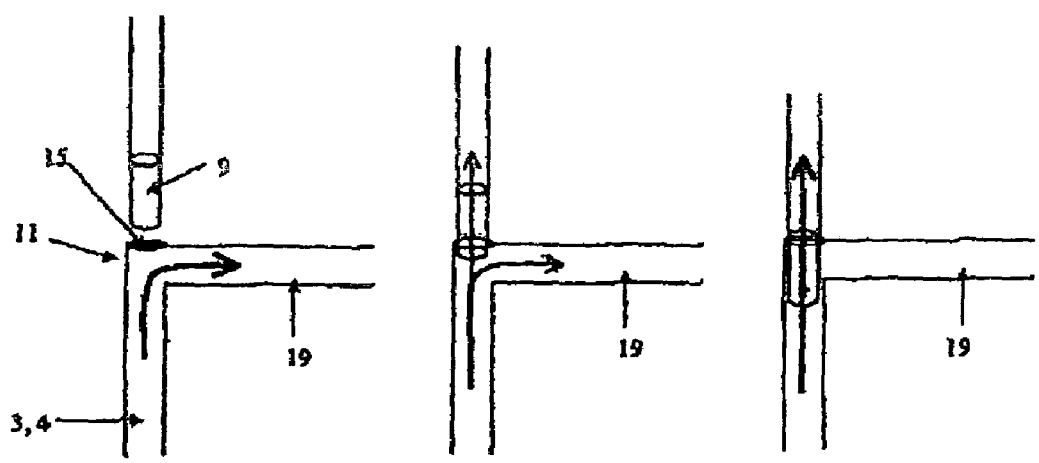
Figure 3:
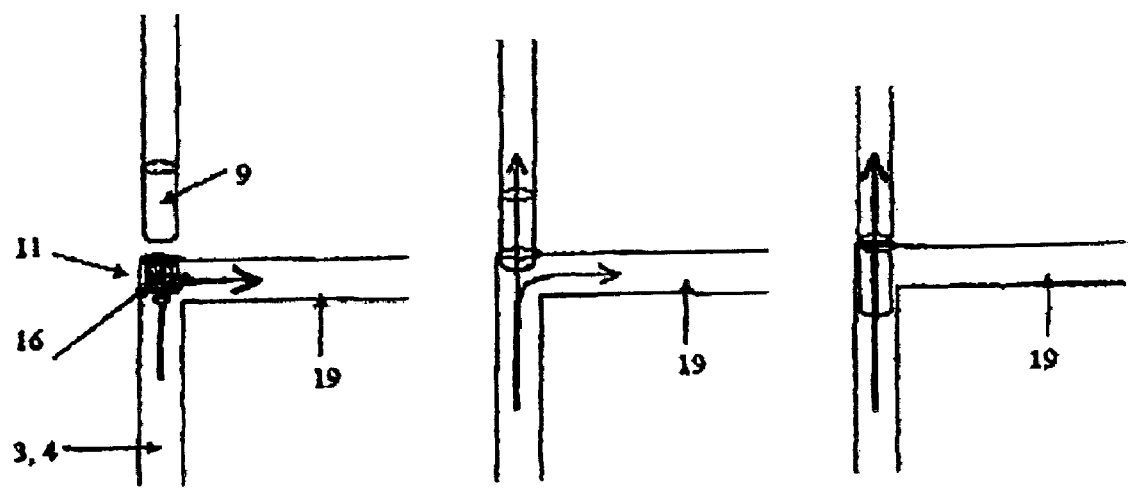

Demonstrated are:

FIG. 1 A schematic representation of two functional modules with an additional functional module marked by dashes;

FIG. 2 A schematic representation of one of a first design examples of portals in the three phases of a connection; and FIG. 3 A schematic representation of one of a second design examples of portals in the three phases of connection.

FIG. 1 shows a schematic representation of a first functional module 1, of a second functional module 2 and, marked by dashes, an additional functional module 18. The functional modules 1, 2 and 18 are filled with body fluids such as, for example, units of a perfusion system with a blood flow, whereby one such functional module can be, for example, a dialysis filter for hemodialysis or an oxygen generator of a heart/lung machine. Herein, for the purposes of the following description, the functional module 1 is a used functional module to be substituted where, for example, the filter is obstructed and is to be substituted; and the functional module 2 is new, which is to take over the function of the functional module 1 for which it is substituting. The dash represented functional module 18 is only an additional module for representing the possibility of also substituting the functional module by another functional module, specifically the module 18.

The functional module 1 comprises a conduit 3 for the extra-corporeal flow of body fluids, which enter from the patient through a feeder line 20 and then the input 7 into the functional module 1 and after it again departs the functional module 1, it is re-circulated to the patient through output 8 and a drainage point 21, which has a conduit 3 passing through the functional module 1 and has one each portal 11 or 12 in two easily accessible locations, which makes possible access to the conduit 3 from the outside. This access to the portals 11 and 12 is in an unused germ free condition closed by a penetrable membrane 15. And, should the occasion arise, the membrane 15 is protected from unintended penetration by a protective cap (not shown here) or a similar sterile covering or by a combination of both.

The functional module 2 reflects the principle of a same design as the functional module 1. Here also, a conduit 4 with an input 5 and an output 6 runs through the entire functional module 2 and two locations easily accessible from the outside and two standardized locations, each provided with portals 13 and 14 which are closed by a membrane 15. In contrast to the functional module 1, the functional module 2 has an air release priming valve in the area of output 6 for aeration of the functional module 2 or for filling it with a fluid. Furthermore, the functional module 2 differs from the functional module 1 by two valve connections 9 and 10 which protrude at the input 5 and output 6 from the housing of the functional module 2 to the extent that they intervene during the mounting of the functional module 2 on the functional module 1 in the portals 11 and 12 of the functional module 1. Moreover, the portals 11 and 12 of the functional module 1 are so constructed that the body fluid circulation is diverted during the complete intervention of the valve connections 9 and 10 in the portals 11 and 12 from the module 1 to module 2, and thus the functional circulation of the module 1 becomes bridged over. The same can also occur during the mounting of an additional functional module 18 on the functional module 2, whereby the functional module 18 again (not shown here) is provided with valve connections, which intervene in the portals 13 and 14 of the functional module 2.

FIG. 2 shows a detailed representation of the first design of the portals 11, 12, 13, and 14 in three phases of the intervention of a valve connection 9. This first design form of the portals 11, 12, 13, and 14 lies in the fact that an angled branching is part of the corresponding conduit 3 or 4, whereby the direction of the flow during the operation of the functional module 1 from the conduits 3 and 4 flows around to the right in the branching section 19, since the way from this phase or, as the case may be, in the normal working condition of the functional module 1 is still closed by a membrane 15. In phase 2 (the middle representation) the valve connection 9 has penetrated the membrane 15 and thus comes to intervene with the portal 11 of the functional module 1. Already at this point, the body fluid flow bifurcates to one straight direction into the functional module 2 and the remaining partial flow into the branching section 19. This condition, nevertheless, exists for only a brief period of time, specifically, just until the valve connection 9 has been completely inserted into the portal 11 as it is shown in the far right representation. That is to say, the valve connection 9 closes the branch section 19 and the flow of the body fluid has been completely diverted to the second function module 2.

FIG. 3 shows an alternative design form of the portals 11, 12, 13, and 14, according to which a valve mechanism in form of a three-way valve (16) is arranged in the branching section, which causes the body fluid flow to be diverted into the second functional module 2 or, as the case may be, into any additional functional module 18, after penetrating the valve connection 9. In this type of design, the valve connection 9 does not need to penetrate so deeply into the portal 16 as is the case in the design form according to FIG. 2, since with the penetration, the attendant obstruction of the branching section 19 in case of the second design form according to FIG. 3 takes place by means of the valve 16.

The invention claimed is:

1. A device for changing and/or docking of first and second functional modules (1 and 2) for the extra corporeal circulation of body fluids, each functional module (1 and 2) provided with at least one body fluid flow permeable (3 and 4) with an inlet (5 and 7) and an outlet (6 and 8), the device comprising:

at least one connecting element (9, 10; 11, and 12) for connecting the conduit (3) of the first functional module (1) to the inlet (5) and the outlet (6) of the second functional module (2) so that the first functional module (1) is bypassed by a fluid-mechanical bridging through the second functional module (2) to maintain the flow of the body fluid, wherein the connecting element (9, 10; 11, and 12) includes a valve connection for the inlet (5) and the outlet (6) of the second functional module (2) and a designated portal in the conduit (3) of the first functional module (1), the valve connection protruding outwardly at the inlet (5) and the outlet (6) of the second functional module (2) to an extent that the valve connections intervene in the respective portals of the first functional module (1) during a mounting of the second functional module (2) on the first functional module (1), the valve connections interacting during the connecting of the first and second functional modules (1 and 2) in each of the respective portals so that the functional circulation of the first functional module (1) is by-passed, wherein the second functional module (2) for connecting with an additional functional module (18) is provided with portals (13 and 14), each of the portals containing an angled branch of the associated conduit (3 and 4) so that the connecting valve closes an axonal branch (19) of the conduit (3 and 4) during a penetration into the assigned portal and diverts the flow of the body fluid into at least one of the second functional module (2) and the functional module (18).

2. The device according to claim 1, wherein the inlet (5) and the outlet (6) of the second functional module (2), each provided with a valve connection which, upon connecting the functional module (1 or 2) with the correspondingly designed portals for preparation of a leak-tight connection, the valve connection can interact with the permeable body fluid.

3. The device according to claim 1, wherein each of the portals is sealed germfree at the outward pointing end in an unused condition by means of a permeable membrane (15).

4. The device according to claim 1, wherein each of the portals is sealed germ free at the outward pointing end by means of a valve (16).

5. The device according to claim 1, wherein each of the portals is maintained germ free or sterile by means of a protective cap or foil.

6. The device according to claim 1, wherein at least one of the outlet (6) of the second functional module (2) and the outlet of the additional functional module (18) is provided with a priming valve (17) for evacuation of air from, or for filling with a fluid, at least one of the second functional module (2) and the functional module (18).

7. The device according to claim 1, wherein each portal contains a valve mechanism by means of which the flow of the body fluids is diverted into at least one of the second functional module (2) and the functional module (18) after the penetration of the valve connections.

8. A device for changing and/or docking of first and second functional modules (1 and 2) for the extra corporeal circulation of body fluids, each functional module (1 and 2) provided with at least one body fluid flow permeable (3 and 4) with an inlet (5 and 7) and an outlet (6 and 8), the device comprising:

at least one connecting element (9, 10; 11, and 12) for connecting the conduit (3) of the first functional module (1) to the inlet (5) and the outlet (6) of the second functional module (2) so that the first functional module (1) is bypassed by a fluid-mechanical bridging through the second functional module (2) to maintain the flow of the body fluid, wherein the connecting element (9, 10; 11, and 12) includes a valve connection for the inlet (5) and the outlet (6) of the second functional module (2) and a designated portal in the conduit (3) of the first functional module (1), the valve connection protruding outwardly at the inlet (5) and the outlet (6) of the second functional module (2) to an extent that the valve connections intervene in the respective portals of the first functional module (1) during a mounting of the second functional module (2) on the first functional module (1), the valve connections interacting during the connecting of the first and second functional modules (1 and 2) in each of the respective portals so that the functional circulation of the first functional module (1) is by-passed, wherein the second functional module (2) for connecting with an additional functional module (18) is provided with portals (13 and 14), each portal containing a valve mechanism by means of which the flow of the body fluids is diverted into at least one of the second functional module (2) and the functional module (18) after the penetration of the valve connections.

\* \* \* \* \*